(12) United States Patent
Hampel

(10) Patent No.: US 8,401,143 B2
(45) Date of Patent: Mar. 19, 2013

(54) ARRANGEMENT FOR THREE-DIMENSIONAL ELECTRON BEAM TOMOGRAPHY

(75) Inventor: Uwe Hampel, Dresden (DE)

(73) Assignee: Helmholtz-Zentrum Dresden-Rossendorf E.V., Dresden (DE)

( * ) Notice: Subject to any disclaimer, the term of this patent is extended or adjusted under 35 U.S.C. 154(b) by 233 days.

(21) Appl. No.: 12/864,164

(22) PCT Filed: Jan. 20, 2009

(86) PCT No.: PCT/DE2009/050000
§ 371 (c)(1),
(2), (4) Date: Jul. 22, 2010

(87) PCT Pub. No.: WO2009/092372
PCT Pub. Date: Jul. 30, 2009

(65) Prior Publication Data
US 2010/0303198 A1  Dec. 2, 2010

(30) Foreign Application Priority Data
Jan. 23, 2008  (DE) .................. 10 2008 005 718

(51) Int. Cl.
*A61B 6/00*  (2006.01)
(52) U.S. Cl. ............................................. 378/10
(58) Field of Classification Search .......... 378/4, 10, 378/12, 16, 19, 21
See application file for complete search history.

(56) References Cited

U.S. PATENT DOCUMENTS

| 4,944,448 A | 7/1990 | Peschmann et al. |
| 5,172,401 A * | 12/1992 | Asari et al. ............ 378/10 |
| 5,745,546 A | 4/1998 | Hell et al. |
| 2004/0109539 A1 | 6/2004 | Apel et al. |
| 2006/0050842 A1 | 3/2006 | Wang et al. |

FOREIGN PATENT DOCUMENTS

| DE | 19510047 A1 | 9/1996 |
| DE | 10240628 A1 | 3/2004 |
| DE | 10356601 A1 | 7/2005 |

OTHER PUBLICATIONS

GE Wang et al.: "Topical Review; Approximate and Exact Cone-Beam Reconstruction With Standard and Non-Standard Spiral Scanning", Physics in Medicine and Biology, Taylor and Fancis Ltd. London, GB, vol. 52, No. 6, Mar. 21, 2007, pp. R1-R13, XP020113255, ISSN: 0031-9155, p. R7.

* cited by examiner

*Primary Examiner* — Courtney Thomas
(74) *Attorney, Agent, or Firm* — Laurence A. Greenberg; Werner H. Stemer; Ralph E. Locher

(57) ABSTRACT

It is an object of the present invention to specify an arrangement for X-ray computed tomography, which allows continuous three-dimensional imaging of the examination object or a partial volume of the examination object at a high temporal and spatial resolution, wherein a high spatial resolution defines both a high resolution within the slice plane and also in the axial direction.

5 Claims, 2 Drawing Sheets

ARRANGEMENT FOR THREE-DIMENSIONAL ELECTRON BEAM TOMOGRAPHY

The invention relates to an arrangement for three-dimensional X-ray computed tomography (X-ray CT) using an electron beam.

Electron beam X-ray computed tomography has been used for a number of years in medical diagnostics, in particular for imaging the beating heart. In the process, an electron beam guided in a vacuum chamber is guided over a circular-arc-shaped metal target by means of an electromagnetic deflection system, as a result of which a fast-moving X-ray focal spot is generated. A circular or circular-arc-shaped X-ray detector arranged with a slight axial offset to the target registers the X-ray radiation transmitted through the examination object. The material distribution in the irradiated slice plane can be calculated from the measurement data by applying tomographic image reconstruction methods.

X-ray computed tomography scanners operating according to the spiral-CT principle are also known and have been used in medicine for a number of years. Here, the object volume is scanned in a three-dimensional fashion by moving the examination object (for example a patient on a couch) in a slow and continuous fashion through the slice plane in the axial direction, while the recording system consisting of X-ray emitter and detector is rapidly rotated around the examination object. This results in a helical profile of the X-ray focal-spot path around the object in the object coordinate system, which is where the name "spiral computed tomography (spiral CT)" for the recording method originates.

The particular advantage of the electron-beam computed-tomography arrangement lies in the high imaging rate that can be achieved, which imaging rate is given as a result of the fast deflectability of the inertia-free electron beam by using alternating magnetic fields. However, in principle this arrangement only allows for the generation of images in an irradiation plane. A transition to a multi-slice or spiral CT is only possible by axial movement of the examination object. However, inertia of the examination object then again limits the recording rate for three-dimensional data. This does not permit fast three-dimensional imaging. The electron-beam computed-tomography arrangements described in documents U.S. Pat. No. 4,352,021A and U.S. Pat. No. 5,504,791A at least allow the electron beam to be guided over different target segments situated in the axial direction. This allows a very fast change of the slice plane, which allows quasi-simultaneous recordings in various slice planes. However, since the slice-plane spacing here is a few millimeters or centimeters as a result of the design of said arrangement, three-dimensional imaging with a high axial resolution, for example smaller than the one-millimeter range, is not possible. Moreover, the X-ray detector in these arrangements is arranged with an axial offset with respect to the target. This means that the scanning X-ray beams are not all situated in one slice plane, and so this results in imaging errors, which make the diagnosis more difficult.

An object of the present invention is to specify an arrangement for X-ray computed tomography, which allows continuous three-dimensional imaging of the examination object or a partial volume of the examination object at a high temporal and spatial resolution, wherein a high spatial resolution defines both a high resolution within the slice plane and also in the axial direction.

In order to achieve this object, an arrangement for electron beam tomography with a fixed and specially shaped target through which radiation can pass and with a fixed X-ray detector is specified. The object is achieved by the features of claim 1. Refinements of the invention are implemented in the dependent claims.

The particular advantage of the invented arrangement for X-ray computed tomography consists of the fact that using it allows spatially and temporally continuous imaging of the attenuation-coefficient distribution and thus of mainly the density distribution within an object at high imaging rate. For this reason, the invented arrangement is suitable for many diagnostic questions in which dynamic processes should be examined. In the biological-medical field these are, for example, examinations relating to perfusion dynamics and motion in humans and animals, or in the technical field these are, for example, questions relating to dynamic material behavior under load or to flow processes in vessels.

The invention will be explained in more detail below on the basis of an exemplary embodiment.

In the associated figures, using the example of a small animal CT scanner,

Figure 1:
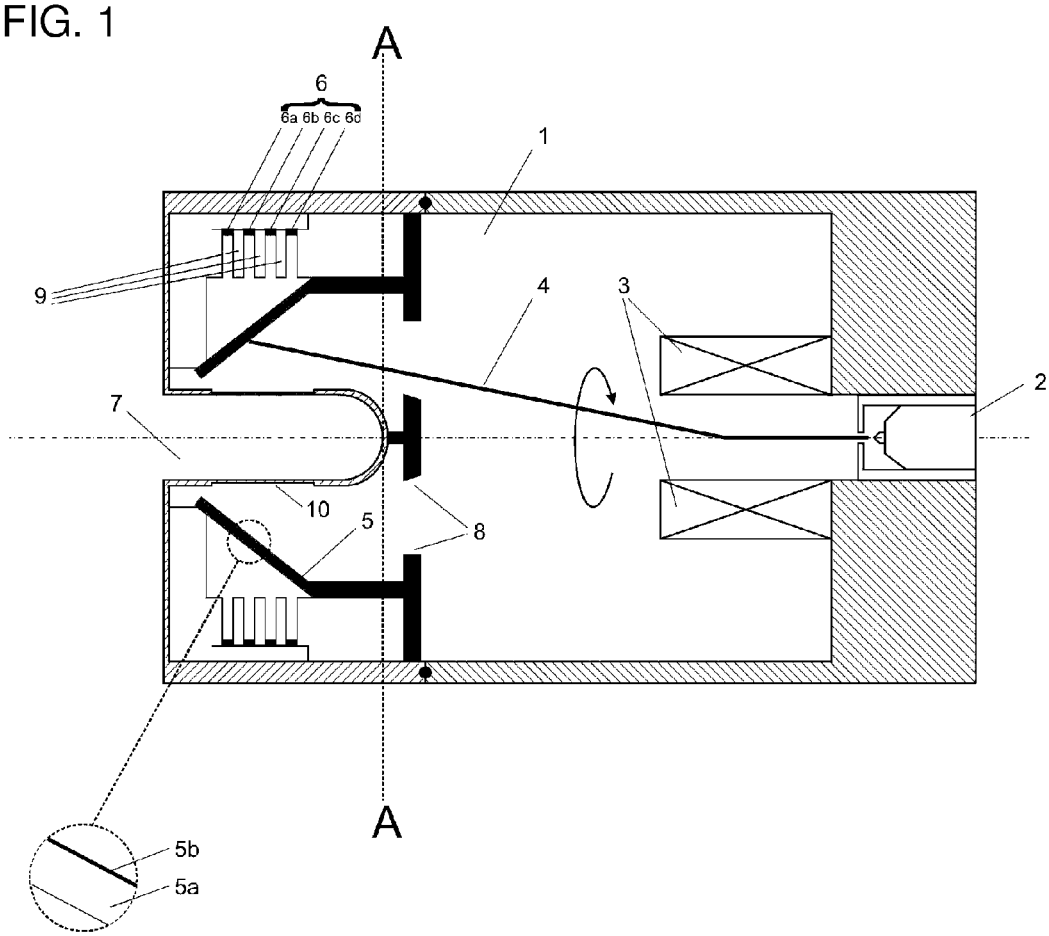
FIG. 1 shows an axial slice through the overall arrangement.
Figure 2:
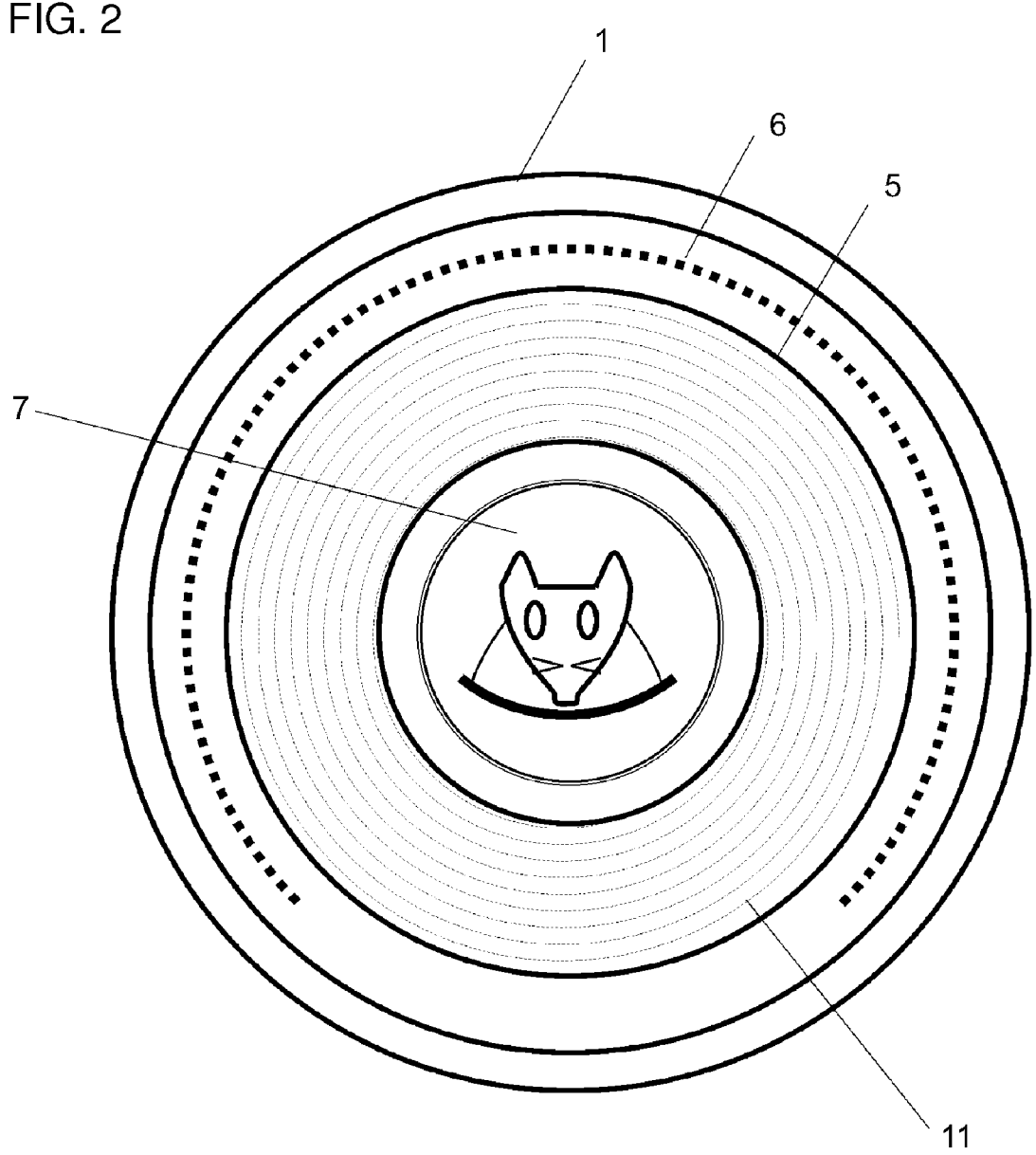
FIG. 2 shows a view of the arrangement along the slice A-A.

The arrangement consists of at least the following components:
- a vacuum chamber 1 that surrounds the electron beam system,
- an electron gun 2,
- an electron-optical system 3 for focusing and deflecting in two dimensions the electron beam 4 emanating from the electron gun 2,
- a target 5 for X-ray beam generation,
- an X-ray detector 6,
- electron beam stops 8,
- a detector collimator 9 for suppressing scattered radiation,
- and further optional components not listed explicitly here, but known to a person skilled in the art, such as sensors for measuring and monitoring important operational parameters (target temperature, quality of the vacuum, electron beam parameters), electronic components for registering measured values, generating high and auxiliary voltages and beam guidance, components for hardening the beam, components for shielding, a couch or holders for the examination object, cooling device for the target.

It is advantageous for the receiving opening for the examination object 7, in which the wall of the vacuum chamber 1 is thinned out in the interior region to form an X-ray beam output window 10.

The target 5 has the shape of a cylindrical ring tapering in the electron beam direction. The target 5 consists of a solid target base body 5*a*, which in turn advantageously consists of a material with a low density and a high thermal conductivity and heat storage capacity (for example compressed graphite), and a thin conversion layer 5*b* made of a material with a high atomic number and density (for example tungsten) applied to the inner side of the target base body 5*a*.

The electron beam 4 emanating from the electron gun 2 is focused on the inner side of the target 5 by the electron-optical system 3. Here, deflection coils of the electron-optical system 2 force the beam onto a spiral-shaped path, and so a spiral-shaped focal-spot path 11 is generated on the inner side of the target 5. Alternatively, it is possible to successively drive the electron beam 4 onto circular paths with different diameters by jump-like changes in the polar beam deflection angle during a continuous circular motion of the beam.

The X-ray detector 6 consists of a plurality of circular-arc-shaped segments (6a, 6b, . . . ), which in turn comprise individual detectors adjoining one another without gaps. The X-ray detector 6 is connected to specialist electronics (not illustrated in the figure), which can very rapidly register and store the signals of the individual detectors of the X-ray detector 6. The angular range of the circular-arc segments 6a, 6b, . . . and the number of circular-arc segments 6a, 6b, . . . are determined according to recognized rules and laws of computed-tomography image reconstruction and are assumed to be known by a person skilled in the art. This results in the required angle of the circular-arc segments of 180° plus the angle of the beam fan of the arrangement. The number of segments arises from the required image quality. Since this imaging method is a cone-beam CT scan, certain image unsharpness results from the undersampling of the three-dimensional projection space brought about thereby. This is reduced with an increasing number of circular-arc segments per axial unit length.

Certain auxiliary elements are a further feature of the arrangement. These include electron beam stops 8 and a detector collimator 9. Additionally, the arrangement can comprise further auxiliary elements that are known to a person skilled in the art and do not constitute essential components within the sense of the invention. The electron beam stops 8 constitute an aperture for the electron beam 4, which prevents the electron beam 4 from being able to hit other elements of the arrangement other than the target 5. These electron beam stops 8 can at the same time be used for beam monitoring, that is to say for example for monitoring the beam flux constancy, by being mounted insulated from the ground potential and by leakage currents being measured by resistors when the electron beam 4 is deliberately guided over these electron beam stops 8.

The detector collimator 9 limits the axial field of view of the detector segments 6a, 6b, . . . to fan-shaped regions and has an axially-symmetric design. The object thereof is to suppress scattered radiation from construction elements in the arrangement.

LIST OF REFERENCE SIGNS

1 Vacuum chamber
2 Electron gun
3 Electron-optical system
4 Electron beam
5 Target
5a Target base body
5b Conversion layer
6 X-ray detector
6a . . . 6d Circular-arc segments of the X-ray detector
7 Receiving opening for the examination object
8 Electron beam stops
9 Detector collimator
10 X-ray beam output window
11 Focal-spot path

The invention claimed is:

1. An arrangement for three-dimensional electron beam tomography, comprising:
   an electron-optical system for generating, focusing and deflecting an electron beam within a vacuum chamber in an electron beam direction;
   a target arranged within the vacuum chamber for decelerating the electron beam and for generating X-ray radiation, the target including a target base body and an applied conversion layer;
   an X-ray detector subdivided into a plurality of circular-arc segments and arranged within the vacuum chamber;
   a receiving opening for an examination object, the target surrounding the receiving opening for the examination object, the target having an inner side;
   electron beam stops arranged within the vacuum chamber; and
   a detector collimator arranged within the vacuum chamber;
   wherein:
   the target is formed as a cylindrical ring tapering in the electron beam direction;
   the circular-arc segments of the X-ray detector surround the target, and the plurality of circular-arc segments of the X-ray detector are arranged at a plurality of axial distances;
   the target is fixed and allows radiation to pass therethrough;
   the X-ray detector is fixed;
   the electron beam is forced into a spiral path by the electron-optical system and thereby generates a spatially spiral-shaped focal-spot path on the inner side of the target or the electron beam is successively forced into circular paths with different diameters by the electron-optical system and thereby generates a spatial focal-spot path that consists of a multiplicity of circles with different diameters on the inner side of the target.

2. The arrangement according to claim 1, wherein the target has a target base body with an inner side, and the target has a conversion layer that is applied to the inner side of the target base body.

3. The arrangement according to claim 1, wherein: the vacuum chamber includes a thinned out wall and other walls, the thinned out wall is thin compared to the other walls of the vacuum chamber, and the thinned out wall forms an X-ray beam output window in the receiving opening for the examination object.

4. The arrangement according to claim 1, wherein the detector collimator is axially symmetric, and the detector collimator limits an axial field of view of the detector segments to fan-shaped regions.

5. The arrangement according to claim 1, wherein the electron beam stops are arranged in a course of the electron beam to ensure that the electron beam hits only the target.

* * * * *